(12) United States Patent
Jestrabek-Hart

(10) Patent No.: US 6,913,583 B2
(45) Date of Patent: Jul. 5, 2005

(54) ORTHOPEDIC DEVICE ALLOWS KNEELING WITHOUT CONTACTING KNEE

(75) Inventor: Bernadette Jestrabek-Hart, Meridian, ID (US)

(73) Assignee: Creations by B J H, LLC, Meridian, ID (US)

( * ) Notice: Subject to any disclaimer, the term of this patent is extended or adjusted under 35 U.S.C. 154(b) by 61 days.

(21) Appl. No.: 10/601,917

(22) Filed: Jun. 19, 2003

(65) Prior Publication Data

US 2004/0260219 A1 Dec. 23, 2004

(51) Int. Cl.$^7$ ................................................ A61F 5/00
(52) U.S. Cl. .............................. 602/16; 602/26; 2/24
(58) Field of Search ............................ 602/16, 23, 26, 602/62; 2/22, 24, 62

(56) References Cited

U.S. PATENT DOCUMENTS

| | | | | |
|---|---|---|---|---|
| 619,665 A | * | 2/1899 | Burt .................................. | 2/24 |
| 1,090,408 A | * | 3/1914 | Peoples ............................ | 2/24 |
| 1,131,816 A | * | 3/1915 | Bassett ............................. | 2/24 |
| 1,136,307 A | * | 4/1915 | Bourdon ......................... | 2/456 |
| 1,138,973 A | * | 5/1915 | Prince .............................. | 2/24 |
| 1,533,907 A | * | 4/1925 | Whipp ............................. | 2/24 |
| 1,796,234 A | * | 3/1931 | Bassett ............................. | 2/24 |
| 2,423,849 A | * | 7/1947 | Patterson ......................... | 2/24 |
| 3,025,526 A | * | 3/1962 | Gino ................................. | 2/24 |
| 3,346,877 A | * | 10/1967 | Zirves .............................. | 2/24 |
| 4,030,489 A | * | 6/1977 | Buckner ......................... | 602/5 |
| 4,144,592 A | | 3/1979 | Larson | |
| 4,490,855 A | * | 1/1985 | Figgie et al. ..................... | 2/24 |
| 4,517,968 A | * | 5/1985 | Greene et al. ................. | 602/27 |
| 4,599,748 A | * | 7/1986 | Garcia ............................. | 2/22 |
| 4,607,628 A | * | 8/1986 | Dashefsky .................... | 602/26 |
| 4,633,529 A | * | 1/1987 | Litz ................................. | 2/22 |
| 4,801,138 A | * | 1/1989 | Airy et al. .................... | 482/112 |
| 4,884,561 A | * | 12/1989 | Letson, Sr. .................... | 602/16 |
| 5,300,016 A | * | 4/1994 | Marlatt ......................... | 602/16 |
| 5,524,292 A | | 6/1996 | Hargens | |
| 5,571,206 A | | 11/1996 | Varn | |
| 5,711,029 A | | 1/1998 | Visco et al. | |
| 5,882,321 A | * | 3/1999 | Fisk ............................. | 602/4 |
| 6,010,474 A | | 1/2000 | Wycoki | |
| 6,315,750 B1 | * | 11/2001 | Gray ........................... | 602/32 |
| 6,427,239 B1 | | 8/2002 | Worden | |
| 6,637,034 B1 | * | 10/2003 | Worden ......................... | 2/24 |
| 6,769,134 B1 | * | 8/2004 | Mendez ......................... | 2/22 |
| 6,799,592 B1 | * | 10/2004 | Reynolds ..................... | 135/74 |

* cited by examiner

Primary Examiner—Henry Bennett
Assistant Examiner—Amanda Wieker
(74) Attorney, Agent, or Firm—Your Intellectual Property Matters, LLC; Robert A. Frohwerk

(57) ABSTRACT

The described Kneepad gives its wearer the advantage of being able to kneel without putting weight on the knee. This allows someone to kneel who may not otherwise be able to do so due to a knee replacement, or some other reason that disallows application of pressure to the knee. The support mechanism is composed of rugged, load-bearing materials, such as metal or plastics. Straps provide various means of adjustment for a correct fit when attached to the thigh of the wearer above the knee. The Kneepad can be quickly and easily removed and reapplied, and does not interfere with walking. An improvement over prior kneepads that placed the knee in contact with the kneeling surface, this invention does not involve such contact, since the thigh area above the knee takes all of the pressure of kneeling. With this invention many people who have not been able to kneel previously, may be able to do so. One alternate embodiment of the invention allows a wearer to lean on a sensitive elbow. Another embodiment transfers the pressure of sitting from the pelvic-gluteal region to the waist and above for wearers recovering from surgery or injury to the lower spine, colorectal or gluteal areas.

9 Claims, 7 Drawing Sheets

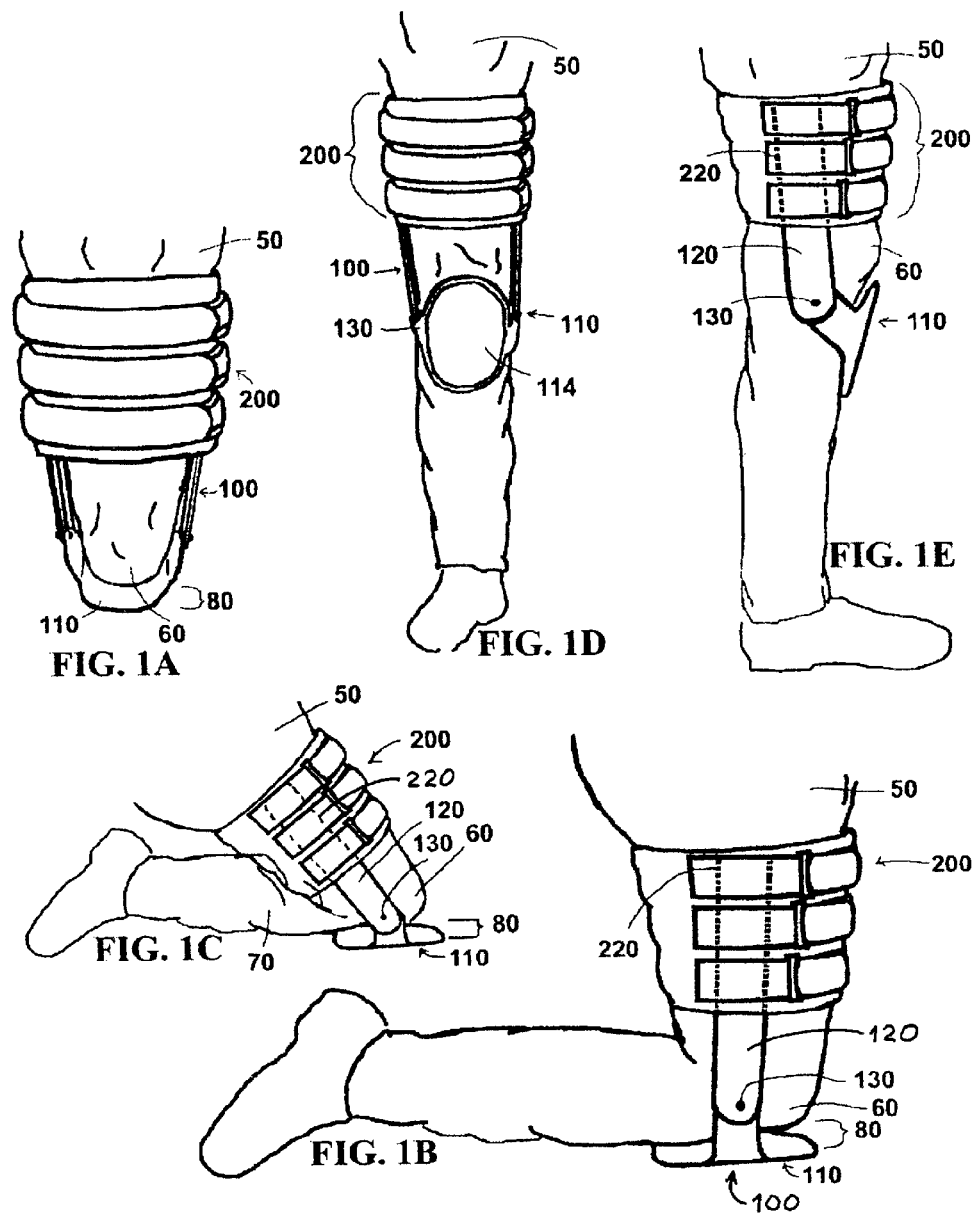

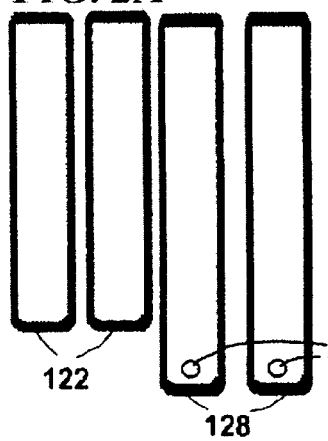
FIG. 2A
FIG. 2B
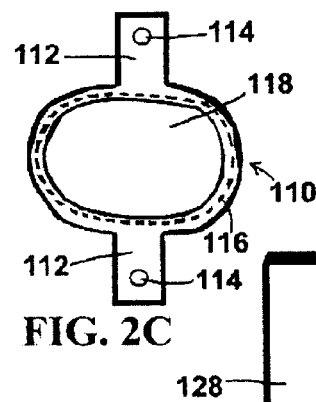
FIG. 2C
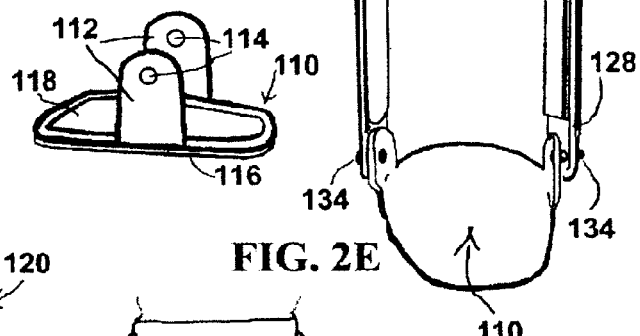
FIG. 2D
FIG. 2E
FIG. 2F
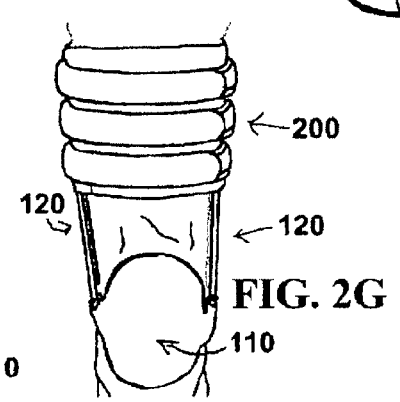
FIG. 2G

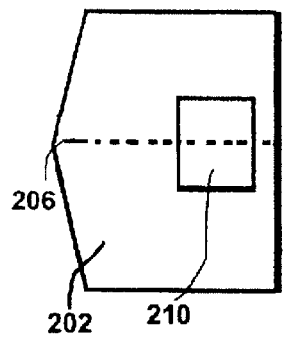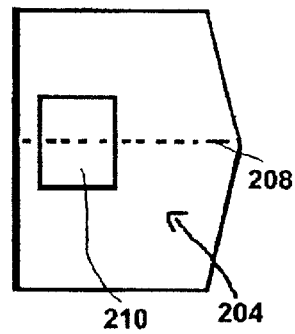# FIG. 3A
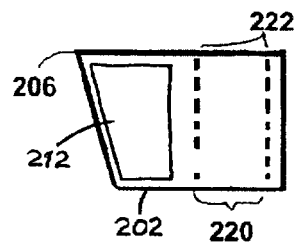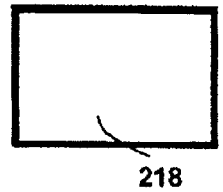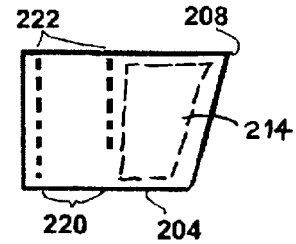
FIG. 3B
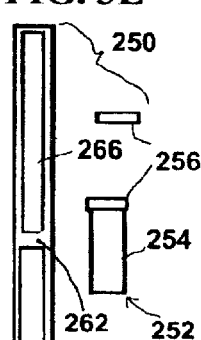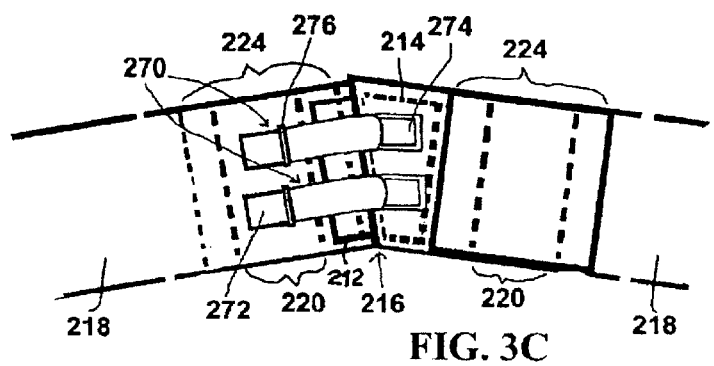
FIG. 3C
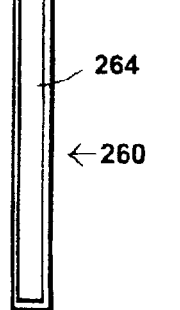
FIG. 3E
FIG. 3D

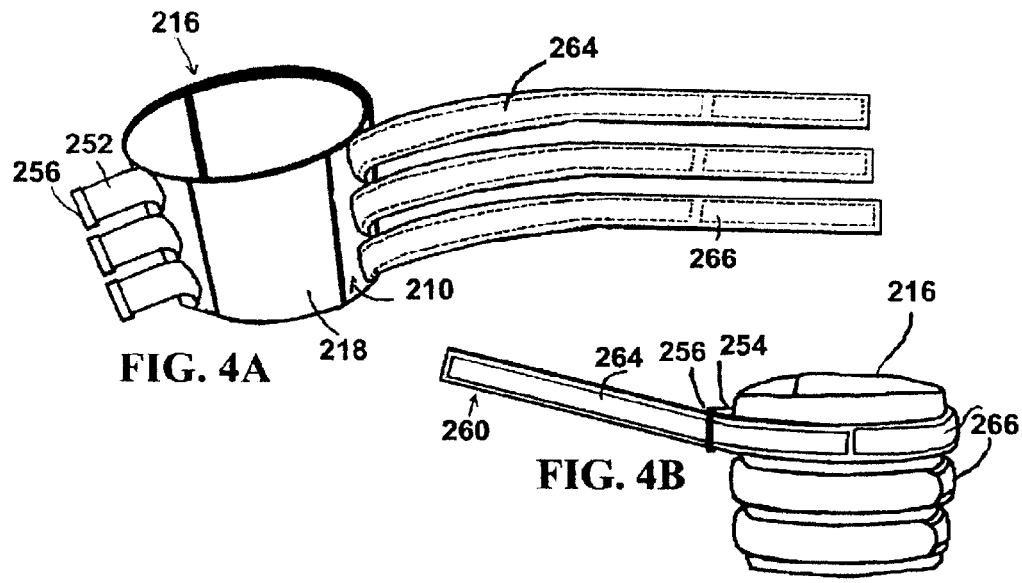
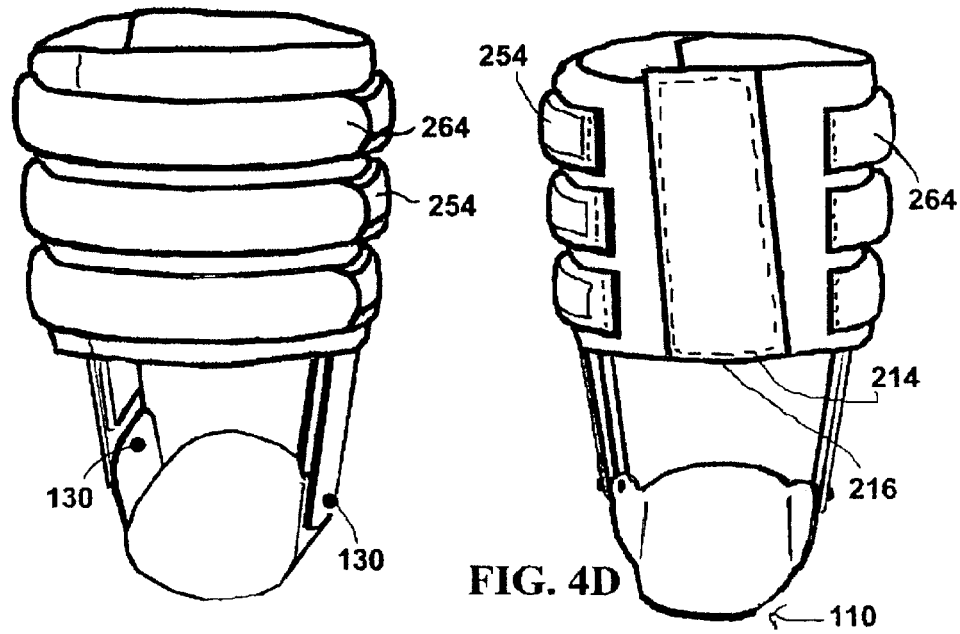

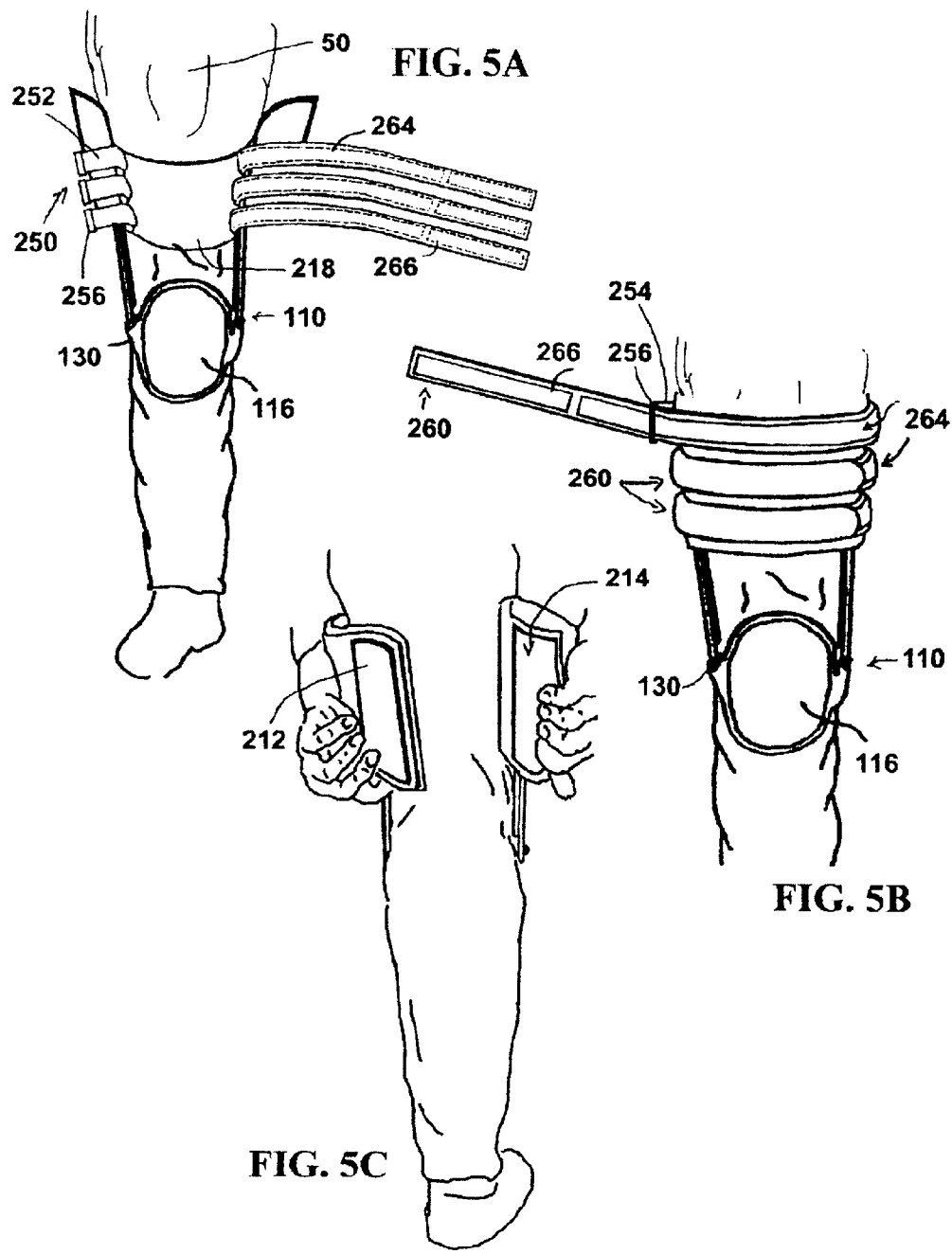

ORTHOPEDIC DEVICE ALLOWS KNEELING WITHOUT CONTACTING KNEE

FIELD OF THE INVENTION

The present invention relates to orthopedic equipment in general. More specifically, the present invention enables a wearer to kneel without actually contacting the surface of the knee, so as to prevent injury and to optimize healing. The invention is adaptable for similar protection of other body parts, especially the elbow, and the pelvic and gluteal region.

BACKGROUND

The knee is a critical part of the body. In addition to its articulation that enables us to stand, walk and sit, the knee allows us to kneel, unless the knee joint or its surface has become overly sensitized or has been replaced. Certain mechanical and structural problems can make the knee too sore to be knelt upon, or the action of kneeling may harm the joint. For some, kneeling is medically prohibited due to the stress placed upon the knee joint. This may occur in a natural knee, but is most often associated with a knee that has been surgically repaired, or replaced with a mechanical one. Lower leg amputees have special concerns when it comes to getting down on ones knee, since a sensitive leg stub may disallow any contact and be incapable of providing support without injury.

Even though a person may know better than to kneel, there are times when it is convenient and perhaps even necessary, for example, when a dropped object rolls under a piece of furniture. Though there may be other ways of retrieving the object, the most straightforward solution often involves kneeling. Some tasks are simply much easier to accomplish when one is able to kneel.

The marketplace offers a variety of knee pads and guards that cushion or shield the knee in the hope of reducing injury. Most of the currently available items have the form of a pad that attaches to the leg by means of a sleeve or by using straps or clips. The pads are made of foam or gel or may be fluid-filled. One example that stands out from the more common devices is a product known as the "Patella-T Orthopedic Fluid-Based Kneepad", described by Visco, et al in U.S. Pat. No. 5,711,029. Although the kneepad covered by that design still touches the knee itself, the device does take special care to cushion the patella (kneecap). Most currently available kneepads are indeed nothing more than a pad; they merely provide a cushion for the knee against impact or load and nothing more. At best, currently available devices simply distribute the load encountered when resting on ones knee over a wider area in an attempt to reduce localized pressure points.

In addition to pads, the existing art describes various forms of guards and shields. Worden's U.S. Pat. No. 6,427,239 shows a knee guard that attaches to the lower leg of the user just above the ankle. In U.S. Pat. No. 4,144,592 a knee guard is described by Larson that shields against lateral impact as well as rearward impact from the front even while explicitly allowing the wearer to kneel in direct contact with the ground or other kneeling surface. Larson's device attaches to the thigh above the protected knee. Though neither of these two devices attach to the knee, both allow the knee to bear the load of the body when in a kneeling position.

The invention described here has advantages over the prior art in that it completely offloads the knee when used in a kneeling position. It applies no pressure whatsoever to the knee and makes no contact with the knee or the leg below the knee. This invention is so protective that lower leg amputees may use it to kneel. Adaptations of the described invention afford similar protection to those who are not able to lean comfortably on an elbow and to those who cannot assume a sitting posture that would apply pressure to the pelvic or gluteal regions.

BRIEF SUMMARY OF THE INVENTION

For purposes of explanation, the present invention initially will be referred to as a kneepad since it satisfies the functional requirements of such a device. As a special class of improved pad for the knee, it is such in function only. The described device is not what would commonly be considered a pad, in the sense that a cushion is a pad, though it does provide similar functionality by distributing pressure away from the protected area. Neither is use of the described invention restricted to protection of the kneecap or knee joint and it should be understood from the outset that the present invention may be extended to the protection of other joints as will be described here. In general, the present invention encompasses a family of orthopedic devices and methods for the protection of any joint that moves between extension and flexion in a hinge-like manner, in particular the knee, elbow, and hip joints and the areas surrounding them.

The function of a kneepad is accomplished by the present invention in that it does not contact or allow any pressure to be exerted on the surface of the knee itself. This device has the unique advantage that it allows its wearer to kneel without making any contact with the knee. It is specifically designed with a means of attachment that encircles the leg above the knee securing the described Kneepad comfortably into place and relieving all of the pressure from the knee. By transferring pressure away from the knee without touching it, the wearer may kneel without applying any load whatsoever to the knee.

The present invention preferably has a means of attachment that encircles the leg above the knee and another support means that extends downward to a pod component that makes contact with the ground when the user kneels. The pod component swivels on its support so as to allow one to kneel with the upper leg perpendicular to the ground or to bend the knee back while kneeling if the wearer is otherwise allowed to bend the knee that far. This swivel also allows one to stand fully upright and to walk while wearing the Kneepad.

The main problem with kneepads in the prior art that is overcome in the present invention is that they all apply pressure to the knee when a person is actually kneeling. A person who cannot have pressure on the knee, previously had no way to kneel. This invention addresses that issue.

BRIEF DESCRIPTION OF THE DRAWINGS

FIGS. 1A–1E show various views of the complete Kneepad of an embodiment of the present invention applied to a leg in various positions, namely, front view kneeling, side view kneeling perpendicularly, side view kneeling in acute position, front view standing, and side view standing.

FIGS. 2A–2G are an exploded view showing rigid parts that compose the support mechanism of an embodiment of the present invention.

FIGS. 3A–3E show the components of the mechanism used for attachment to the leg in an embodiment of the present invention with details for the assembly of the components.

FIGS. 4A–4D are perspective views of the assembled components showing the attachment mechanism that wraps around the upper leg in the preferred embodiment of the invention.

FIGS. 5A–5C are perspective views showing the Kneepad being attached to a leg and operation of the quick release capability in the preferred embodiment.

DETAILED DESCRIPTION

Figures 6A, 6B, 6C:
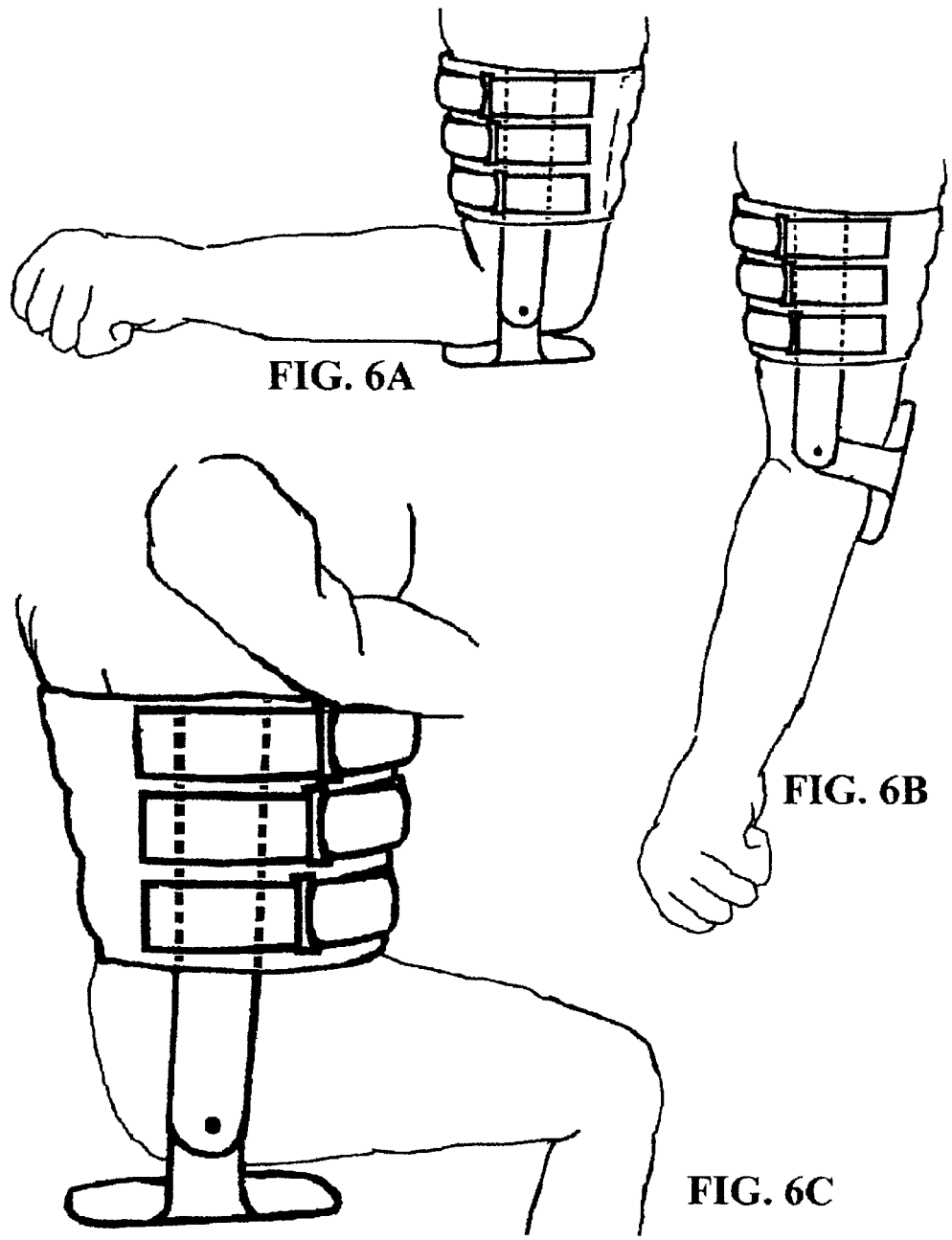
FIGS. 6A–6C show alternate embodiments of the invention in use to protect an elbow and a spinal-gluteal region.

The present invention is a specialized form of kneepad that allows a person to kneel without making any contact with, or applying any pressure to, the knee itself. As will be described, the preferred embodiment of the invention is composed of two major subunits, the first being a support mechanism that also provides protection of the knee, while the second is a cuff for attachment of that support mechanism to a body.

Referring to FIGS. 1A–1E, one will note the support mechanism 100 that is attached to the thigh 50 of the wearer by cuff 200. The support mechanism 100 allows the wearer to rest comfortably in a kneeling position as shown in front view FIG. 1A and side view FIG. 1B while maintaining some physical separation 80 between the knee 60 and the inside of the pod 110 as it rests on a floor or other kneeling surface. The separation 80 will typically be adjusted to be at least 1 inch. In this position, all of the pressure of kneeling is transferred from the pod 110, through the pod support arms 120 to the cuff 200; that pressure being taken by the thigh 50, completely bypassing the knee 60. If the wearer leans backward, as in FIG. 1C, the weight may be shifted to the lower leg 70 and to the back of the thigh 50, but there is still no pressure applied to the knee 60.

The pod 110 is pivotably mounted to the support arms 120 at pivot 130. The freely operating pivot 130 allows the pod 110 to rest lightly against the lower leg 70 when the wearer is standing, as in front view FIG. 1D and side view FIG. 1E. When the wearer kneels, as in FIGS. 1A and 1B, the pivot 130 allows the pod 110 to drop into the position needed to provide support. If the wearer desires to lean backward, and is otherwise able to do so, as in FIG. 1C, the pivot 130 will allow that as well, giving full support as necessary.

Detailed construction of the support mechanism 100 is shown in FIGS. 2A–2G. This description begins with the pod 110 that makes contact with the kneeling surface. The suggested shape of the pod 110 is shown in FIG. 2C, that being generally oval in the preferred embodiment. This shape provides stability when kneeling upon it and keeps it in place as weight is applied to it. The pod 110 of the preferred embodiment uses a plate made of aluminum. The underside of the pod 110 is covered with a protective contact pad 116 which may be made of hard foam, leather or something similar depending upon the environment in which it will be used. The upper side of pod 110 receives an inner pod cushion 118 which may be made of a foam or gel material. This will cushion the knee in case of severe shock or impact to the pod 110 that would cause the inner pod cushion 118 to come into contact with the knee 60. Holes 114 are placed in the ears 112 of the pod 110 which are then bent upward to a 90-degree angle to form the completed pod 110 shown in FIG. 2D.

It is recognized that other materials and manufacturing processes will produce other pods that still meet the requirements for this component. Specific applications and environments may suggest other forms for pod 110. For example, a contoured pod may be molded from an impact resistant plastic to act as a larger shield to the knee while allowing the user to rock or roll sideways. Some users may prefer that the outer pod contact surface 116 allow them to slide without difficulty across a floor surface whereas other applicants will want a non-skid surface. Other users may require that the outer pod contact surface 116 not scratch or scuff the surface that is knelt upon. Many variations are possible within the scope of the invention as described.

The function of the support arms 120 is to connect the pod 110 to the cuff 200. In this role the support arms 120 must be capable of static support of nearly the entire body weight of the user. Additionally, the support arms 120 must allow sufficient margin to avoid collapse due to dynamic loads such as the compression encountered when dropping onto the pod 110 or lateral failure due to bending as might occur if the wearer leaned to the side while resting on the pod 110. These requirements establish some minimal parameters for the structural materials that compose the support arms 120.

Another requirement of the support arms 120 is that, for ease of use, they be adjustable in length to accommodate variations among users. Any adjustment means must not weaken the overall structure of the support arms 120, that is, the entire assembly must qualify under the same conditions of load-bearing and rigidity.

In the preferred embodiment, the two pod support arms 120 are each made up of a sandwich of the subcomponents shown in FIGS. 2A and 2B. This sandwich includes a shorter arm member 122 and a longer arm member 128. Between these arm members are a shorter adjustment panel 124 and a mating longer adjustment panel 126. The arm members 122 and 128 are made of a lightweight metal or high-strength plastic, which may be one that is reinforced with carbon or other fibers. Those possessing basic skills in the engineering of materials will recognize that there are many materials that are suitably stiff and yet resilient enough for use in these subcomponents, and are capable of withstanding the loads to which they will be subjected. It is these sandwiched support arm members 120, shown fully assembled in FIG. 2E, that will be inserted into sleeves 220 (FIGS. 1B and 1E) in the cuff 200 to transfer the weight of the kneeling user from the pod 110 to the thigh 50 so as to bypass the knee 60.

The sandwiched support arm members 120 are designed to allow for fine adjustment over a wide range in their length to accommodate individual users. It is this adjustment, necessitated by variations in the size and shape of knees and thighs, which sets the space 80 to clear the knee 60 from the inside of the pod 110. The location of the upper end of the support arm members 120 will be determined by contact between the shorter arm members 122 and the top of the inside of sleeves 220 in the cuff 200. In the preferred embodiment, adjustment panels 124 are cut from the hook side of a hook and loop type of fastener and are attached to the shorter support arm members 122, while adjustment panels 126 are cut from the loop side of a hook and loop type of fastener and attached to the longer support arm members 128. The attachment of these adjustment panels (124 and 126) to their respective support arm members (122 and 128) may be accomplished by any of various bonding methods or adhesive agents as understood in the art to provide sufficient strength for the specific loads to be encountered. The shorter support arm 122 with its applied adjustment panel 124 is releasably engaged with the longer support arm 128 through its applied adjustment panel 126 with an offset appropriate to adjust the overall length of the resulting sandwiched support arms 120 for the needs of the individual user of the Kneepad. Sufficient overlap area between the adjustment panels (124 and 126) provides more than enough friction to support the required load. These sandwiched support arms 120 are slid into sleeves 220 of the cuff 200 and can be taken out and adjusted as needed at any time.

Figure 7A:
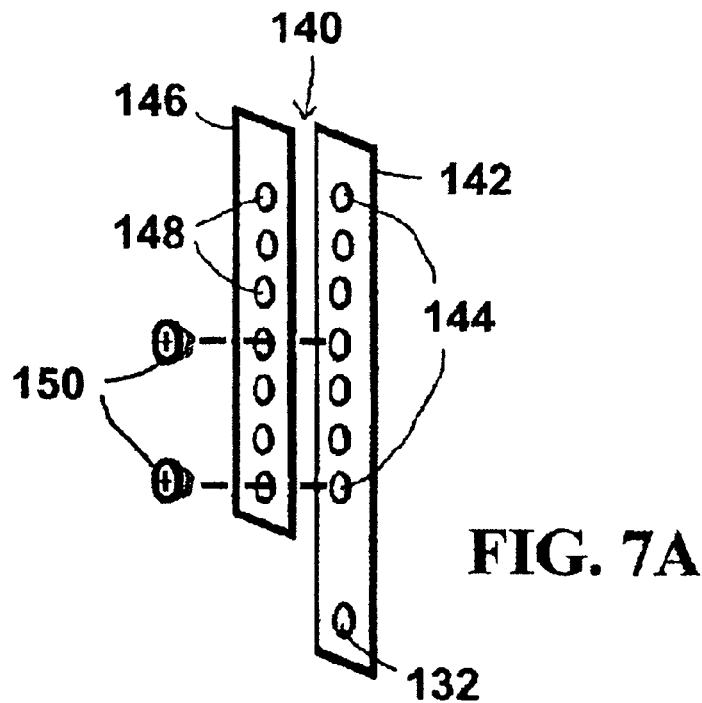
FIGS. 7A and 7B depict alternative construction methods for the support arms that connect the pod to the cuff.

Though a hook and loop coupling system has been described for the preferred embodiment, those familiar with the mechanical arts will recognize other couplers that are in a sense slideably adjustable as well as capable of supporting the necessary vertical load required in this application. One approach, shown in FIG. 7A, provides a series of longitudinally spaced threaded mounting holes 144 in the longer arm member 142. A setscrew 150, having a flush-mounting head, is inserted in a beveled through-hole 148 of the shorter arm member 146. With an appropriate longitudinal offset between arm members 142 and 146 to provide the proper overall length of the support arm 140, setscrew 150 is tightened into threaded hole 144. When completely assembled, this support arm 140 replaces the sandwiched version of pod support arms 120 described above (FIG. 2E) while eliminating adjustment panels 124 and 126. Pivot hole 132 provides the connection to pod 110.

Figure 7B:
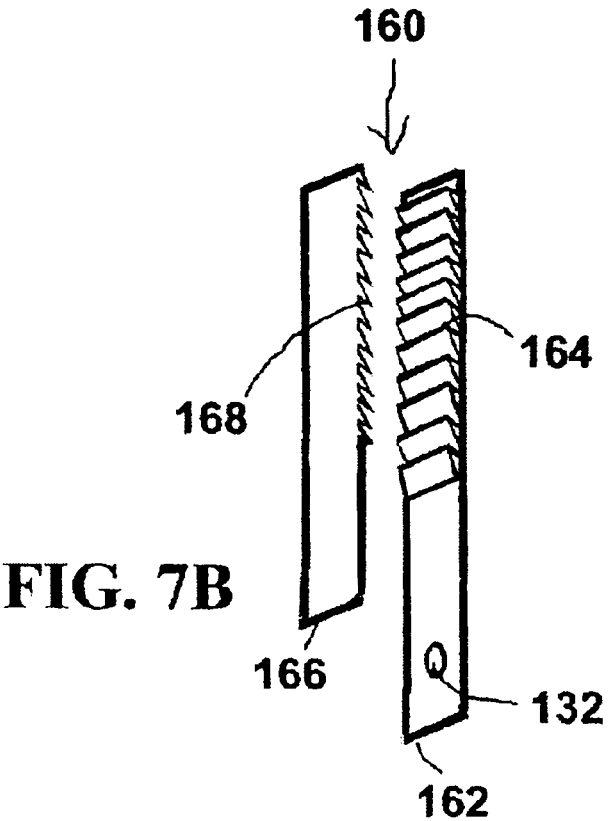

Another alternative coupler that may offer a finer adjustment of incremental changes in length is made from a pair of complementary saw-toothed plates as shown in FIG. 7B. The engagement of a set of upward-facing teeth 164 in a longer adjustment plate 162 with a corresponding set of downward-facing indentations 168 in shorter adjustment plate 166 locks the two members in a certain relative position against an applied vertical load. By pulling on the distal end of the longer adjustment plate 166, the locking means is released and the length can be adjusted as desired. Such a system, especially with aggressively undercut teeth, can provide significant load-bearing capability so as to establish sufficient friction to support necessary body weight in compression. Only a small force orthogonal to the faces of adjustment plates 162 and 166 is required between the two plates to maintain their interlock; sufficient force is supplied by a snug fit of sleeve 220. This small force can be easily released to allow plates 162 and 166 to slide one against the other when pulled in order to lengthen a support arm 160 that has been so constructed. Again, the assembled support arm 160 with pivot 132 replaces pod support arm 120 of FIG. 2E.

The pod 110 attaches to the support arms 120 at pivots 130. Each of these pivots 130 is the result of a rivet 134 placed through hole 114 in an ear 112 of the pod 110, which is then attached to the longer support arm 128 through hole 132. It is obvious that a bolt or other fastener may be substituted for the rivet 134, as long as the two pieces so attached are allowed to move back and forth easily. FIGS. 2F and 2G as well as FIGS. 1C–1E show the need for this swivel. It allows the user to stand, to kneel either with the upper body oriented vertically or leaning back, while wearing this Kneepad.

Because of the location of the support arms 120 as they hang along the side of the leg and the fact that they have some width, the Kneepad provides some protection against lateral impact. The width of the support arms 120 in the preferred embodiment is about 2-inches, but may be increased to provide a larger side shield, or reduced to minimize the weight of the device itself. Since the pod 110 folds up in front of the knee 60 when the user is standing, the described Kneepad also provides some protection against frontal impact.

The construction of the cuff 200, which is the means of attachment to the thigh 50, is described in FIGS. 3A–3E, illustrating suggested patterns for the subcomponents. A wide selection of material may be used as long as it is strong enough to hold up under the stresses that will be encountered, and soft, non-elastic and breathable for comfort. The intermediate section 218 that attaches to the two cuff end tabs 202 and 204 needs to be made of a strong elastic material. In use this intermediate section 218 will lie on top of the thigh 50, above the knee 60. The belt straps 250 will tighten over this intermediate section 218, thereby holding the entire cuff 200 securely to the thigh 50. From FIG. 3A one works toward FIG. 3B by folding the cuff end tabs 202 and 204 in half along their respective midlines 206 and 208 and stitching all around the outside except in the area where stitching 222 will create sleeve 220 for reception of the pod support arms 120 described in reference to FIG. 1E. Reinforcement panels 210 are applied to the cuff end tabs 202 and 204 to act as a stop for the upper end of the sleeves 220. Cuff end tab 202 is sewn to the left end of the elastic intermediate section 218 and cuff end tab 204 to the right end. For a stronger joint, it may be desirable to capture intermediate section 218 inside the cuff end tabs 202 and 204 prior to folding and stitching them.

To make the cuff 200 fit more securely as well as for greater comfort, it has pads 224, shown in FIGS. 3C and 3D, attached to its inside to cover the width of the sleeve 220 and extending a little beyond. These pads 224 are made of a soft material such as foam or gel. In use they act as a buffer over the area next to the thigh 50 against the straight and hard pod support arms 120 which are held in sleeves 220. Pads 224 also mold to the shape of the leg for an improved fit.

In FIG. 3B, the left cuff end tab 202 has a piece of the loop side of a hook and loop type of fastener, shown as loop fastener 212, attached on the outside at the end more distant from the intermediate section 218. A piece of the hook side of a hook and loop type of fastener, denoted as hook fastener 214, is attached to the inside of the right cuff end tab 204 at the far end away from intermediate section 218. These two fasteners 212 and 214 will then connect at the overlap 216 as shown in FIGS. 3C and 3D to form the cuff 200 into a continuous band.

The user may don the Kneepad with the thigh 50 oriented horizontally, as when in a seated position. In this situation the elastic intermediate section 218 will be laid over the thigh 50 just above the knee 60, then the hook and loop fastener (212 and 214) will be connected to close the band around the thigh 50 forming the overlap 216 at the underside of the thigh 50. The Kneepad is then adjusted through the pod support arms 120 so that the pod 110 will be spaced appropriately distant from the knee 60 when the leg is bent, this separation 80 typically being at least 1 inch. Once the Kneepad is initially in place, it must be tightened to maintain a secure fit when the wearer kneels. There are many designs that can be used to tighten the cuff 200 to avoid slippage. The method chosen for the preferred embodiment is shown in FIGS. 3D and 3E where belts 250 are used to tighten the cuff 200. The number of belts 250 used will typically be three, as shown in these illustrations, but may vary depending on the height of the cuff 200 required to accommodate the weight and body size of individual users.

A belt 250 has a shorter belt section 252 and a longer belt section 260. These may be made of any suitable belting material. In the preferred embodiment, webbing has been selected for this purpose. The shorter belt section 252 is formed by sewing one end of a short piece of webbing 254 so as to capture a rectangular loop 256. The other end of the shorter belt section 252 will be attached to the right cuff end tab 204 as shown in FIGS. 3D and 4A.

The longer belt section 260 is made from a long piece of webbing 262 to which is attached a long piece of the loop side 264 of a hook and loop type of fastener and a short piece of the hook side 266 of a hook and loop type of fastener each on the same face of the long piece of webbing 262. The end of the resultant longer belt section 260 having long piece of the loop side 264 of a hook and loop type of fastener will be attached to the left cuff end tab 202 as shown in FIGS. 3D and 4A with the webbing surface of the longer belt section 260 facing the left cuff end tab 202 and the active surface having the hook and loop fasteners will face away from the left cuff end tab 202. Multiple such belts 250 as mentioned above will be attached in this manner. To tighten the cuff 200 around the thigh 50 of the user, after the two fasteners 212 and 214 have been connected as described above to form a continuous band, the longer belt section 260 will be pulled through the corresponding rectangular loop 256 as shown in FIG. 4B and then folded back, pulled tight and connected to itself by mating of the opposing hook and loop sections 264 and 266. FIG. 4C shows the front of the freestanding Kneepad unattached to a person whereas FIG. 4D shows the rear view.

FIGS. 5A–5C illustrate how to attach the cuff 200 to the thigh 50 above the knee with the pod 110 of the Kneepad lying along the leg properly located below the knee when in a standing position. The elastic intermediate section 218 is first placed on the thigh 50 in front of the leg, then the ends of hook and loop fasteners 214 and 212 are pulled tight and connected behind the thigh 50 to form overlap 216 in FIG. 5C, as was taught in the construction details above with regard to FIGS. 3C and 3D Then the belts 250 are pulled across the elastic intermediate section 218, the ends of the longer belt sections 260 passed through the corresponding rectangular loops 256 of the shorter belt sections 252, pulled tight and attached back over themselves as depicted in FIG. 5B. To remove the Kneepad quickly, simply pull the hook fastener 214 away from the loop fastener 212 to release the overlap 216 at the back of the thigh 50 as shown in FIG. 5C. This quick release feature is the reason for this kind of attachment at the rear. This also allows the user to remove the Kneepad by lifting it away from the front without any obstruction at the rear as would be the case with a common sleeve type of construction that must be put on and taken off by slipping over the lower leg and foot. This kind of rear attachment also allows for some degree of adjustment for legs of different girth. After taking the Kneepad off as illustrated in FIG. 5C, the user can loosen the belts 250, attach the overlap 216 together again, and tighten as needed without needing to take the belts 250 out of the rectangular loops; simply loosening the belts 250 saves time in reinstalling the Kneepad.

Some users may present an unusually large load to the cuff 200, either due to body weight or the likelihood that they will bend the knee 60 to an extremely acute angle. This puts great stress on overlap 216 that may cause the hook and loop closure to disconnect. To overcome this unfortunate circumstance, which would allow the user to drop onto the knee 60, a set of optional reinforcement straps 270 may be installed as shown in FIG. 3C. Reinforcement strap 270 is shorter than, but otherwise constructed similar to, belt 250 shown in FIG. 3E. The short end 272 of reinforcement strap 270 with captive rectangular loop 276 is attached to the outside of cuff 200 opposite pad 224 near left cuff end tab 202. The long end 274 of reinforcement strap 270 will have a section of the loop portion of a hook and loop fastener and a section of hook portion. Near the end with the loop portion the long end 274 of reinforcement strap 270 is attached to right cuff end tab 204 in a position corresponding to the placement of the short end 272. When used, the long end of reinforcement strap 274 with its hook portion will be pulled through rectangular loop 276 and back onto itself so as to connect the hook and loop fastener, thereby giving extra strength to the overlap 216.

In the preferred embodiment each of the two (or optionally three) described sets of fasteners is implemented as a hook and loop fastener. It is readily recognized that many other closure mechanisms may be used. Alternatives include but are not limited to various combinations of belts, buckles, hooks, latches, laces and the like. The first set of fasteners provides for the closure of cuff 200, at overlap 216, into a continuous band encircling the leg. In addition to offering small incremental adjustments to the fit, the described hook and loop application also provides for quick release of the connection, and leaves an open cuff that may be easily lifted away from the thigh. The second set of fasteners is used to tighten the cuff 200 around the thigh 50 once the first set of fasteners has been secured. The construction of this second set of fasteners has fewer requirements and therefore more options are available for materials and format of the fastening system without sacrificing the described features of the preferred embodiment.

Those familiar with the art of support structures will recognize that the two pod support arms 120 may incorporate some form of shock absorber or spring-loaded suspension element. This could be used to cushion the wearer in case of a fall or any quicker than expected drop onto ones knees.

While the present invention has been described as a kneepad, those who may not have a knee in the literal sense, such as leg amputees, may use it without modification. The described invention could be applied whether the leg is terminated in a stub at, or below, or near but above, where the knee would be, as long as there is sufficient area at the thigh to support the user's weight.

Additionally, the described technique may be applied in a similar manner for protection of other flexible (or missing) joints or the body parts near those joints.

The technique taught by the present invention may be applied in general to transfer weight from any region of the body that is sensitive to pressure to another adjacent portion of the body that can withstand the load. Any joint that moves between extension and flexion in a hinge-like manner is a ready candidate for such protection. FIG. 6A shows the technique applied to an elbow in flexion and FIG. 6B to an elbow in extension. An application protecting the pelvic and gluteal regions is shown in FIG. 6C. Here the user is offered relief through a torso-mounted device that allows one to be seated without putting pressure on the sitting bones (ischial tuberosities), pelvis, lower spine, gluteus, or other potentially sensitive anatomy in the region as in situations following various forms of surgery or injury.

Although the preferred embodiment has been described for use by humans, it may also further be adapted for use on other animals.

Though the present invention has been described with reference to a preferred embodiment, various modifications will be apparent to those skilled in the art.

Therefore, it is not intended that the invention be limited to the disclosed embodiment or its details, and variations can be made within the spirit and scope of the appended claims.

I claim:

1. An orthopedic device for transfer of pressure from a sensitive knee area to an adjacent load-bearing thigh, without connection to a leg below the knee, the orthopedic device comprising:
   (a) a pod that interfaces to a load-bearing contact surface;
   (b) a support means having a length and a means of adjustment of said length, an upper end and a lower end, said pod being pivotably attached to said support means at said lower end; and
   (c) an attachment means for attachment of the orthopedic device to the load-bearing thigh and connected to said support means at said upper end.

2. The orthopedic device of claim 1 wherein said support means comprises a pair of support arms, each support arm of said pair of support arms in turn comprising:
   (a) a rigid shorter support arm member;
   (b) a shorter adjustment panel comprising either of a hook or loop portion of a hook and loop fastener, said shorter adjustment panel being adhered to said rigid shorter support arm member;
   (c) a rigid longer support arm member providing at one end a means of pivotable attachment to said pod;
   (d) a longer adjustment panel comprising the portion of a hook and loop fastener that is complementary to that of said shorter adjustment panel, said longer adjustment panel being adhered to said rigid longer support arm member; and
   (e) said rigid shorter support arm member being coupled to said rigid longer support arm member by releasably engaging said shorter adjustment panel with said longer adjustment panel with a longitudinal offset appropriate to adjust said length of said support means.

3. The orthopedic device of claim 1 wherein said means of adjustment of said length is by disconnecting a hook and loop fastener and reconnecting said hook and loop fastener with a longitudinal offset between the hook portion and the loop portion of said hook and loop fastener.

4. The orthopedic device of claim 1 wherein said support means comprises a pair of support arms, each support arm of said pair of support arms in turn comprising:
   (a) a rigid shorter support arm member being an attachment plate having a first set of longitudinally spaced holes;
   (b) a rigid longer support arm member being an attachment plate having a second set of longitudinally spaced holes nearer one end and a means of pivotable attachment to said pod at the other end; and
   (c) at least one threaded fastener having a head that is beveled or otherwise capable of being recessed when threadably engaged;
   wherein one of said first or second set of longitudinally spaced holes is a set of through-holes being beveled or otherwise shaped so as to receive the at least one threaded fastener;
   the other of said first or second set of longitudinally spaced holes is a set of threaded holes so as to engage the threaded portion of the at least one threaded fastener;
   the spacing of the holes in said set of through-holes being either the same as, or a small integral multiple of, the spacing of the holes in said set of threaded holes;
   said length of said support means being established by coupling of said rigid shorter support arm member to said rigid longer support arm member by placing the faces of said rigid shorter support arm member and said rigid longer support arm member in contact with one another with a longitudinal offset appropriate to adjust said length of said support means, realigning as appropriate so that at least one of said set of threaded holes aligns with a near hole from said set of through holes, the at least one threaded fastener then being inserted into the near hole from said set of through holes and threadably engaged with the corresponding threaded hole.

5. The orthopedic device of claim 1 wherein said support means comprises a pair of support arms, each support arm of said pair of support arms in turn comprising:
   (a) a rigid shorter support arm member being an attachment plate having a first set of longitudinally spaced horizontal ridges with a cross section being that of downward-facing saw teeth; and
   (b) a rigid longer support arm member being an attachment plate having a second set of longitudinally spaced horizontal ridges with a cross section being that of upward-facing saw teeth nearer said upper end and a means of pivotable attachment to said pod at said lower end;
   wherein the downward-facing saw teeth of said rigid shorter support arm member are engaged with the upward-facing saw teeth of said rigid longer support arm so as to adjust said length of said support means, the support arm members being thus coupled are inserted into a sleeve of said attachment means, said sleeve providing sufficient force orthogonal to the ridged faces of the coupled support arm members to prevent them from disengaging one from the other.

6. A method that allows a person to kneel as if on a knee without contact of said knee to a kneeling surface, and without connection to any portion of a body below said knee, the method comprising:
   (a) attaching a support structure to a thigh above said knee; and
   (b) moving the person into a kneeling position such that contact with said kneeling surface is made by a pod pivotably attached to the distal end of said support structure so as to provide a protective space between said pod and said knee, thereby transferring the load presented by the kneeling person from said kneeling surface directly to the thigh, by means of said pod and said support structure associated with said pod, completely bypassing said knee.

7. The method of claim 6 wherein the protective space is between about ½ and 1-inch.

8. A method of transferring a load from a pressure-sensitive knee area of a body to a load-bearing thigh adjoining said knee area, wherein said load is generated as if said pressure-sensitive knee area were to rest upon a support surface, said transfer of the load being accomplished without contact between said pressure-sensitive knee area and said support surface, and without connection to any portion of the body below said knee area, the method comprising:

(a) attaching a support structure to said load-bearing thigh adjoining said knee area; and (b) moving the body into a position as if said pressure-sensitive knee area were to rest upon said support surface in a manner of kneeling such that contact with said support surface is made by a pod pivotably attached to the distal end of said support structure so as to provide a protective space between said pod and said pressure-sensitive knee area, thereby transferring the load presented by the body upon said support surface from said support surface directly to said load-bearing thigh adjoining said knee area, by means of said pod and said support structure associated with said pod, completely bypassing said pressure-sensitive knee area.

9. The method of claim 8, wherein the protective space is between about ½ and 1-inch.

* * * * *